US009833469B2

(12) United States Patent
Utecht et al.

(10) Patent No.: US 9,833,469 B2
(45) Date of Patent: Dec. 5, 2017

(54) COMPOSITIONS AND METHODS TO AFFECT SKIN IRRITATION

(71) Applicants: Ronald E. Utecht, Volga, SD (US); Therese M. Downey, Sioux Falls, SD (US); Miri Seiberg, Princton, NJ (US); Stanley S. Shapiro, Roseland, NJ (US)

(72) Inventors: Ronald E. Utecht, Volga, SD (US); Therese M. Downey, Sioux Falls, SD (US); Miri Seiberg, Princton, NJ (US); Stanley S. Shapiro, Roseland, NJ (US)

(73) Assignees: Alumend, LLC, Sioux Dalls, SD (US); WavePharma, LLC, New Orleans, LA (US)

( * ) Notice: Subject to any disclaimer, the term of this patent is extended or adjusted under 35 U.S.C. 154(b) by 0 days.

(21) Appl. No.: 15/387,138

(22) Filed: Dec. 21, 2016

(65) Prior Publication Data

US 2017/0182086 A1 Jun. 29, 2017

Related U.S. Application Data

(60) Provisional application No. 62/271,591, filed on Dec. 28, 2015.

(51) Int. Cl.

| | |
|---|---|
| ***A61K 31/737*** | (2006.01) |
| ***A61K 8/73*** | (2006.01) |
| ***A61F 13/84*** | (2006.01) |
| ***A61Q 19/08*** | (2006.01) |
| ***A61K 31/05*** | (2006.01) |
| ***A61K 9/00*** | (2006.01) |
| ***A61K 8/34*** | (2006.01) |

(52) U.S. Cl.

CPC ........ *A61K 31/737* (2013.01); *A61F 13/8405* (2013.01); *A61K 8/347* (2013.01); *A61K 8/736* (2013.01); *A61K 9/0014* (2013.01); *A61K 31/05* (2013.01); *A61Q 19/08* (2013.01); *A61K 2800/75* (2013.01); *A61K 2800/782* (2013.01)

(58) Field of Classification Search

CPC ...... A61K 31/737; A61K 8/347; A61K 8/736; A61F 13/8405

See application file for complete search history.

(56) References Cited

U.S. PATENT DOCUMENTS

| | | | | |
|---|---|---|---|---|
| 6,451,773 | B1 * | 9/2002 | Oester | A61K 9/0014 428/401 |
| 2002/0172672 | A1 | 11/2002 | Seiberg et al. | |
| 2003/0206958 | A1 | 11/2003 | Cattaneo et al. | |
| 2005/0283004 | A1 * | 12/2005 | Wei | A61K 8/736 536/20 |
| 2008/0200948 | A1 * | 8/2008 | Utecht | A61K 9/0048 606/214 |

FOREIGN PATENT DOCUMENTS

| | | | |
|---|---|---|---|
| WO | 9209636 | A1 | 6/1992 |
| WO | WO-2008094675 | * | 8/2008 |

OTHER PUBLICATIONS

Encyclopedia of Children'S Health, Contact dermatitis, Mar. 19, 2011 [retrieved on Feb. 14, 2017). Retrieved from the Internet: <URL: http://web.archive.org/web/20110319005612/http://www.healthofchildren.com/C/Contact-Dermatitis.html> entire document.

Notification of Transmittal of the International Search Report and the Written Opinion of the International Searching Authority, or the Declaration in PCT/US2016/068060 dated Feb. 24, 2017; 15 pages.

* cited by examiner

*Primary Examiner* — Jianfeng Song

(74) *Attorney, Agent, or Firm* — Shawn P. Foley; Janine M. Susan; Bruce D. Jobse

(57) ABSTRACT

Compositions are described that contain treated chitosan, modified chitosan and/or modified and treated chitosan for use in formulations for skin, hair and nails, and in compositions and methods of reducing topical agent-induced skin irritation and inflammation.

5 Claims, No Drawings

COMPOSITIONS AND METHODS TO AFFECT SKIN IRRITATION

CROSS-REFERENCE TO RELATED APPLICATIONS

This application claims the benefit of and priority to U.S. Provisional Application No. 62/271,591, filed Dec. 28, 2015, which is incorporated herein by reference in its entirety for all purposes.

BACKGROUND

Skin irritation is caused by a wide range of conditions, including allergies, medication, cosmetics, and diseases. Skin irritation results in a rash, which is a visible change in the color or texture of the skin. The skin may become red, itchy, bumpy, chapped, flaky, with hives, or otherwise irritated.

Inflammation of the skin is known as dermatitis. Contact dermatitis is a common cause of skin irritation. Contact rashes occur upon a contact with an agent that causes a reaction. Such agents include, but are not limited to, cosmetic and beauty products, drugs and medications, soaps, detergents, dyes (e.g. in clothing), metals (e.g. nickel in jewelry), chemicals (e.g. in rubber, elastic, or latex), poisonous plants (e.g. poison oak, poison ivy, or poison sumac), environmental toxicants, irritants of botanical origin (e.g. plant parts and plant extracts), irritants of marine origin (e.g. "red tide" or excessive algae bloom), urine and fecal irritants (e.g. agents that induce diaper rash), minerals, transdermal delivery agents and devices (e.g., agents that transfer active ingredients through the skin into the bloodstream such as creams, ointments, lotions, sprays, gels and the like, or devices like microneedles, patches, ultrasound devices, iontophoresis devices and the like), adhesives, foods and other irritants. The contact with, or exposure to the irritating agents could be accidental, or expected, and could be of a single event or multiple, or repetitive events.

Irritant contact dermatitis from plants could be induced mechanically or chemically. The common mechanical plant irritants include thorns, spines, glochids, trichomes, and sharp-edged leaves. Many plant-based chemical irritants are unknown yet, but known agents include calcium oxalate, protoanemonin, isothiocyanates, bromelain, diterpene esters, alkaloids, and other chemical irritants such as naphthoquinone and acids.

Diaper rash (diaper dermatitis) is the persistent compromise of the epidermal barrier, at the macroscopic or microscopic level, with or without infection (e.g. *C. albicans*). The initial stage of diaper rash is induced by contact with digestive enzymes that are present in infant feces, and in particular chymotrypsin. It is further exacerbated by the skin irritating activity of other fecal and urine enzymes, wetness (including diaper hydration and diaper friction), with the possible additional irritation by microbial and fungal agents.

It is desired to provide a prophylactic treatment i.e. to reduce the severity of or to eliminate skin irritation induced by a contact with an irritating agent. It is also desired to provide a treatment to reduce the severity of or to eliminate skin irritation induced after a contact with a skin irritant.

Topical preparations are used to treat skin with a need and provide health and cosmetic benefits thereto. Topical agents include topical medications and skin care products in such forms as balms, creams, gels, oils, lotions, patches, ointments, sprays and the like. They contain an active ingredient with a desired activity, and excipients, which may include e.g. thickeners, preservatives or fragrances. Numerous topical formulations are prescribed by physicians, while many others are available over-the-counter and as cosmetics (e.g. antibacterial and antifungal preparations, anti-inflammatory and pain-relief preparations, cleansing and moisturizing agents, and beautifying and anti-aging agents). Unfortunately, some of these topical preparations induce adverse or undesirable effects such as skin irritation and sometimes allergic reactions, while providing their benefits.

Retinoids are a class of natural and synthetic compounds that include vitamin A and its related chemicals. Retinoids like retinoic acid, retinol (and vitamin A precursors), and their derivatives are used in numerous skin care products, and serve as the "gold standard" active ingredients for "anti-aging" skin care and acne treatment. Retinoids affect the dermis, the epidermis and skin appendices, enhance skin health and wellness, decrease fine lines, even skin color, improve texture, tighten pores, and stimulate blood flow and collagen production. Retinoids are also very effective anti-acne compounds and have efficacy in treating psoriasis.

Unfortunately, many individuals cannot tolerate retinoids because they can be irritating and drying. Retinol and retinoic acid and their derivatives induce redness, scaliness, itching, burning and drying in a dose-responsive manner. Increasing retinoids concentrations, therefore, would enhance epidermal and dermal benefits and reduce the signs of skin aging, but would also increase skin irritation.

The cosmetic and pharmaceutical industries are constantly seeking solutions to reduce topical agent-induced irritation, including retinoid-induced irritation, which would enable (i) an increase in the effective dose of the topical agent without inducing the irritating side effects, or (ii) a reduction in the effective dose of the topical agent without reducing the cosmetic or therapeutic efficacy while reducing the irritating side effects.

SUMMARY OF THE INVENTION

In one or more aspects, the present invention is directed to compositions and methods for reducing topical agent-induced skin irritation and inflammation.

In one or more features of this disclosure, the compositions of these teachings include (a) at least one skin irritating topical agent, and (b) at least one treated chitosan, modified chitosan, modified and treated chitosan or a mixture or combination thereof, where (i) each chitosan exhibits changes in one or more chemical, physical and/or performance properties or characteristics relative to a corresponding untreated or unmodified chitosan, (ii) the treated, modified or treated and modified chitosan is in a non-particulate form, (iii) the modified chitosan comprises one or more charged group, lipophilic group, hydrophilic group, cationic group, or anionic group, which is non-polymeric, and which is covalently bound to chitosan, (iv) the treated chitosan comprises one or more charged group, lipophilic group, hydrophilic group, cationic group, or anionic group, which is non-polymeric, and which ionically interact with chitosan or which is hydrogen bonded to chitosan and where (v) the composition provides a reduction in skin irritation, and/or a reduction in skin inflammation, and/or a reduction in irritant-induced IL-1$\alpha$ secretion after contact with the composition as compared with a control composition comprising the skin irritating topical agent but not the chitosan. In one or more instances, the modifying group, i.e. charged group, lipophilic group, hydrophilic group, cationic group or anionic group is covalently bound to one or more amines of chitosan. In one or more instances, the treating group, i.e.

charged group, lipophilic group, hydrophilic group, cationic group or anionic group interacts ionically with one or more amines of chitosan or is hydrogen bonded to one or more amines, one or more alcohol groups or one or more ether groups (i.e., acetal) of chitosan. In one or more instances of the composition, the lipophilic group is an alkyl group. The alkyl group can be a straight chain alkyl or a branched chain alkyl group containing 4 to 30 carbons. In one or more instances of the composition, the non-polymeric anion is phosphate, citrate, pyro-phosphate, sulfate, iodide, bromide, chloride, nitrate, nitrite, oxalate, acetate, fluoride, chlorate, bromate, chlorite, formate, hydrogen phosphate, or dihydrogen phosphate. In one or more instances of the composition, the charged group is succinate (anionic), amino ethane (cationic), or amino propane (cationic). In one or more instances of the composition, the hydrophilic group is an alcohol. The alcohol can be ethanol or propanol.

In one or more instances of the compositions, the skin irritating topical agent includes but is not limited to, cosmetic agents (e.g. anti-aging agents like retinoids, retinoid derivatives, retinoid precursors, chemical peels, anti-oxidants, botanical extracts and the like), therapeutic agents or therapeutic dermatological ingredients (e.g. anti-acne treatments like salicylic acid or benzoyl peroxide, actinic keratosis treatments like 5-fluoro-uracil or imiquimod, Rosacea treatments like azaleic acid or metronidazole, psoriasis treatments, wound treatments, wart treatments, anti-parasitic treatments like ivermectin, antibiotics, anti-viral agents, anti-fungal agents, steroids, non-steroidal anti-inflammatory agents, analgesics, and the like), cleansing agents, soaps and detergents (e.g. sodium hydroxide, which is found e.g. in soaps, detergents, cleaning products, adhesives, paint removers and disinfectants), disinfectants (e.g. potassium hydroxide, which is found e.g. in disinfectants and sterilizing agents), antiseptics, deodorants, antiperspirants, antimicrobial agents (e.g. anti-bacterial agents, anti-viral agents, anti-parasitic agents, anti-fungal agents like azole compounds such as ketoconazole, and the like), insecticides, skin protectants, fragrances, dyes, sunscreens, depilatory agents, hair growth agents such as minoxidil, dandruff control agents, shaving and after-shaving agents, solvents (found e.g. in paint remover, nail polish removers, topical alcohol products), paint removers, nail-polish remover, adhesives, preservatives, transdermal-delivery agents and devices, acids, bases, minerals, and the like.

In one or more examples of the compositions, cosmetic agents include, but are not limited to, anti-aging agents, lightening agents, darkening agents, beautifying agents (e.g. lipstick, eye shadow, color-corrector, "make-up" compositions, rouge, eye-liner, mascara and the like), retinoids, retinoid derivatives, retinoid precursors, retinoid active metabolites, chemical peels, anti-oxidants, botanical extracts, or their compositions or combinations thereof.

In one or more examples of the compositions, therapeutic agents include, but are not limited to, acne therapeutic agents, rosacea therapeutic agents, actinic keratosis therapeutic agents, psoriasis therapeutic agents, anti-inflammatory agents, anti-bacterial agents, anti-fungal agents, anti-viral agents, anti-parasitic agents, anti-wart agents, wound healing and wound care agents, hair-growth agents, retinoids, or their compositions or combinations thereof.

In one or more examples of the compositions, the precursors and derivatives of retinoids include, but are not limited to, retinol, retinal, retinyl esters, tretinoin (retinoic acid), Vitamin A and its esters, isotretinoin, alitretinoin, etretinate, acitretin, adapalene, bexarotene, and tazarotene and the like, and chemically modified versions of these (e.g. retinol-palmitate or other compounds that will generate the active retinoid or its active metabolites on the skin by either enzymatic or non-enzymatic reactions), or chemically modified versions of thereof, or combinations thereof.

In some examples of the compositions, the retinoids, retinoid precursors or retinoid derivatives comprise about 0.001-5% W/V of the total weight of the composition. In other instances the retinoids, retinoid precursors or retinoid derivatives comprise about 0.01-1% W/V of the total weight of the composition, and in yet other instances the retinoids, retinoid precursors or retinoid derivatives comprise about 0.04-0.5% W/V of the total weight of the composition.

The specific concentrations of the retinoid in the compositions would depends on factors such as, but not limited to, the type of the retinoid, the specific activity of the retinoid, the desired biological effect of the retinoid, the profile of side effects of the retinoid, the type of the modified chitosan, the concentration of the modified chitosan, the age, gender, skin type and body site of the treated skin, and the like.

In one or more examples of the compositions, the treated, modified or modified and treated chitosan is applied in an amount of about 0.0001-5% W/V of the total weight of the topical composition. In another instance the treated, modified or modified and treated chitosan is applied in an amount of about 0.001-3% W/V of the total weight of the topical composition. Yet in another instance the treated, modified or modified and treated chitosan is applied in an amount of about 0.5-2% W/V of the total weight of the topical composition.

The specific concentrations of the treated, modified or modified and treated chitosan in the compositions would depend on factors such as the concentration and specific activity of the topical irritating agent(s), the specific treatment and/or modification of the chitosan, the age, gender skin type and body site of the treated skin, and the like.

In one or more instance, the modified chitosan is covalently modified with an alkyl group. In another instance, the alkyl modified chitosan is covalently modified with an alkyl sulfonic acid. In yet another instance, the alkyl sulfonic acid is octane sulfonic acid.

In one or more instances, the methods of this invention include reducing and/or ameliorating skin irritation and/or topical inflammation induced by a topical agent and/or reducing irritant-induced IL-1$\alpha$ secretion, by applying to the skin a composition including (a) an amount of at least one skin irritating topical agent, and (b) an amount of at least one treated chitosan, or modified chitosan, or modified and treated chitosan or a mixture or combination thereof, effective to reduce, and/or to ameliorate the topical agent-induced skin irritation.

In one or more examples of the methods, the skin irritating topical agent includes, but is not limited to, cosmetic agents (e.g. anti-aging agents like retinoids, retinoid derivatives, retinoid precursors, chemical peels, anti-oxidants, botanical extracts, lightening agents, darkening agents, color cosmetics (e.g. lipstick, mascara, eye-liner, rouge, eye-shadow, color corrector, "make-up" compositions, and the like), therapeutic agents/therapeutic dermatological ingredients (e.g. anti-acne treatments like salicylic acid or benzoyl peroxide, actinic keratosis treatments like 5-fluoro-uracil or imiquimod, Rosacea treatments like azaleic acid or metronidazole, psoriasis treatments, wart treatments, wound healing and wound care agents, hair-growth agents, anti-parasitic treatments like ivermectin, antibiotics, anti-viral agents, anti-fungal agents, anti-inflammatory agents (e.g. steroids, corticosteroids, glucocorticoids, non-steroidal anti-inflammatory agents and the like), analgesics, cleansing agents, soaps and detergents (e.g. sodium hydroxide, which is found e.g. in soaps, detergents, cleaning products, adhesives, paint removers and disinfectants), disinfectants (e.g. potassium hydroxide, which is found e.g. in disinfectants and sterilizing agents), antiseptics, deodorants, antiperspirants, antimicrobial agents (e.g. anti-bacterial agents, anti-viral agents, anti-parasitic agents, anti-fungal agents like azole compounds such as ketoconazole, and the like), insecticides, skin protectants, fragrances, dyes, sunscreens, depilatory agents, hair growth agents such as Minoxidil, dandruff control agents, shaving and after-shaving agents, solvents (found e.g. in paint remover, nail polish removers, topical alcohol products), paint removers, nail-polish remover, adhesives, preservatives, transdermal-delivery agents and devices, acids, bases, minerals, and the like.

In one or more examples of the methods, cosmetic agents include, but are not limited to, anti-aging agents, lightening agents, darkening agents, beautifying agents (e.g. lipstick, eye shadow, color corrector, "make-up" compositions, rouge, eye-liner, mascara and the like), retinoids, retinoid derivatives, retinoid precursors, retinoid active metabolites, chemical peels, anti-oxidants, botanical extracts, color cosmetics, or their compositions or combinations thereof.

In one or more examples of the methods, therapeutic agents include, but are not limited to, acne therapeutic agents, rosacea therapeutic agents, psoriasis therapeutic agents, actinic keratosis therapeutic agents, anti-inflammatory agents, wound healing and wound care agents, anti-bacterial agents, anti-fungal agents, anti-viral agents, anti-parasitic agents, anti-wart agents, retinoids, or their compositions or combinations thereof.

In one or more examples of the methods, the precursors and derivatives of retinoids include, but are not limited to, retinol, retinal, retinyl esters, tretinoin (retinoic acid), Vitamin A and its esters, isotretinoin, alitretinoin, etretinate, acitretin, adapalene, bexarotene, and tazarotene and the like, and chemically modified versions of these (e.g. retinol-palmitate or other compounds that will generate the active retinoid or its active metabolites on the skin by either enzymatic or non-enzymatic reactions), chemically modified versions thereof or combinations thereof.

In one or more examples of the methods, the skin irritating topical agent is retinoids, retinoid precursors or retinoid derivatives in an amount of about 0.001-5% W/V of the total weight of the composition. Yet in other examples of the methods, the skin irritating topical agent is retinoids, retinoid precursors or retinoid derivatives in an amount of about 0.01-1% W/V of the total weight of the composition. Yet in other examples of the methods, the skin irritating topical agent is retinoids, retinoid precursors or retinoid derivatives, in an amount of about 0.04-0.5% W/V of the total weight of the composition.

In one or more examples of the methods, the treated, modified or modified and treated chitosan is applied in an amount of about 0.0001-5% W/V of the total weight of the topical composition. Yet in other examples of the methods, the treated, modified or modified and treated chitosan is applied in an amount of about 0.001-3% W/V of the total weight of the topical composition. Yet in other examples of the methods, the treated, modified or modified and treated chitosan is applied in an amount of about 0.5-2% W/V of the total weight of the topical composition.

The specific concentrations of the treated, modified or modified and treated chitosan in the compositions would depend on factors such as the concentration and specific activity of the topical irritating agent(s), the specific treatment and/or modification of the chitosan, the age, gender skin type and body site of the treated skin, and the like.

In one or more instance, the said modified chitosan is covalently modified with an alkyl group. In other instances, said alkyl modified chitosan is covalently modified with an alkyl sulfonic acid. In yet other instances, the alkyl sulfonic acid is octane sulfonic acid.

In yet another instance, the present invention is directed to methods for reducing skin irritation, and/or inflammation, and/or IL-1$\alpha$ secretion, which are induced by contacting exogenous agents.

In one or more instances, the methods of the present invention are directed to prevent or reduce skin irritation when a contact with an irritant is expected.

In other instances, the methods are directed to post-exposure topical treatment, for reducing the severity or eliminating the irritating or inflammatory reaction that was induced by the exogenous agent.

In one or more instances, the contact with, or the exposure to the exogenous agents could be accidental, while in other instances it could be expected. The contact with the irritating agent could be of a single event or it could be of multiple events or of repeated events. An example of an expected, repeated event could be e.g. the continuous exposure to urine and fecal secretions that are contained by a diaper. An example for a single and unexpected event could be e.g. a contact with poison ivy, poison sumac, or poison oak, or a contact with jewelry that contains e.g. nickel.

In one or more examples of the methods, the exposure to an exogenous agent could include, but is not limited to, exposure to environmental toxicants, irritants of botanical origin (e.g. plant parts and plant extracts), irritants of marine origin (e.g. "red tide" or excessive algae bloom), irritants of microbial origin, irritants of fungal origin, irritants of parasitic origin, urine and fecal irritants (e.g. enzymes and agents that induce diaper rash, e.g. continuous and excessive wetness, pH higher than that of normal healthy skin, or enzymes such as trypsin and chymotrypsin), metals (e.g. nickel in jewelry), acids, bases, minerals, cleansing agents, soaps and detergents, chemicals, foods, contact-dermatitis-inducing agents, cosmetic and beauty products, drugs and medications, therapeutics, disinfectants, antiseptics, antimicrobial agents, anti-fungal agents, anti-viral agents, anti-parasitic agents, anti-bacterial agents, anti-inflammatory agents, insecticides, analgesics, anti-aging agents, skin protectants, sunscreens, deodorants, antiperspirants, depilatory agents, shaving agents, after-shaving agents, hair growth agents, dandruff control agents, fragrances, dyes (e.g. in clothing), chemicals (e.g. in rubber, elastic, or latex), poisonous plants (e.g. poison oak, poison ivy, or poison sumac), transdermal delivery agents and devices, solvents, adhesives, paint removers, nail-polish remover, foods, preservatives, sterilizing agents, UV irradiation, transdermal-delivery agents, transdermal delivery devices and the like, or their compositions or combinations thereof.

In one or more examples of the methods, the plant parts or plant extracts are plants that cause a contact or allergic dermatitis, such as but not limited to, poison ivy, poison oak, or poison sumac.

In one or more examples of the methods, the urine irritants and/or fecal irritants cause diaper rash.

In one or more examples of the methods, the metals are used in jewelry, and include but are not limited to, nickel.

In one or more examples of the methods, cosmetic agents include, but are not limited to, anti-aging agents, lightening agents, darkening agents, beautifying agents, retinoids, retinoid derivatives, retinoid precursors, retinoid active metabolites, chemical peels, anti-oxidants, botanical extracts, color cosmetics, or their compositions or combinations thereof.

In one or more instances of the methods, therapeutic agents include, but are not limited to, acne therapeutic agents, rosacea therapeutic agents, actinic keratosis therapeutic agents, psoriasis therapeutic agents, wound care and wound healing agents, anti-inflammatory agents, anti-bacterial agents, anti-fungal agents, anti-viral agents, anti-parasitic agents, anti-wart agents, retinoids, or their compositions or combinations thereof.

In one instance, the methods to prevent or reduce irritation and inflammatory response comprise of the topical application, before exposure to the exogenous irritant, of at least one treated chitosan, modified chitosan, modified and treated chitosan or a mixture or combination thereof, where (i) each chitosan exhibits changes in one or more chemical, physical and/or performance properties or characteristics relative to a corresponding untreated or unmodified chitosan, and where (ii) the composition provides a protective activity that would reduce the irritation and inflammation induced by the contact with the irritating agent.

In another example, the methods to reduce irritation and inflammatory response after a contact with the exogenous irritant comprise of the topical application of at least one treated chitosan, modified chitosan, modified and treated chitosan or a mixture or combination thereof, where (i) each chitosan exhibits changes in one or more chemical, physical and/or performance properties or characteristics relative to a corresponding untreated or unmodified chitosan, and where (ii) the composition provides an activity that would reduce the irritation and inflammation previously induced by the contact with the irritating agent.

In one or more examples of the methods, the treated, modified or modified and treated chitosan is applied in an amount of about 0.0001-5% W/V of the total weight of the topical composition. Yet in other examples of the methods, the treated, modified or modified and treated chitosan is applied in an amount of about 0.001-3% W/V of the total weight of the topical composition. Yet in other examples of the methods, the treated, modified or modified and treated chitosan is applied in an amount of about 0.5-2% W/V of the total weight of the topical composition.

The specific concentrations of the treated, modified or modified and treated chitosan in the compositions would depend on factors such as the concentration and specific activity of the topical irritating agent(s), the specific treatment and/or modification of the chitosan, the age, gender skin type and body site of the treated skin, and the like.

In one or more instance, the said modified chitosan is covalently modified with an alkyl group. In another instance, said alkyl modified chitosan is covalently modified with an alkyl sulfonic acid. In yet another instance, the alkyl sulfonic acid is octane sulfonic acid.

DETAILED DESCRIPTION OF THE INVENTION

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

A "topical irritating agent" is a compound, composition or formulation that, upon contact with the skin of a subject, causes irritation, inflammation and/or IL-1α secretion.

A "therapeutic agent" is a compound, composition or formulation comprising an "active agent(s)", which is a compound or composition that has a specific pharmacological effect. A therapeutic agent is "pharmaceutically acceptable", meaning that it is suitable for administration to a subject for a stated purpose. Such stated purpose can include the prevention, treatment or mitigation of a disease or condition that affects the structure or function of the body, tissue(s) or cell(s) of a subject. Irrespective of whether a therapeutic agent may or may not cause harm (e.g. skin irritation or inflammation) by its administration to a subject, it may be pharmaceutically acceptable if benefits of the therapeutic agent outweigh its risks. In one aspect, a therapeutic agent is pharmaceutically acceptable if it meets the requirements of an applicable regulatory agency, such as the US Food and Drug Administration, or any other applicable regulatory body, or if it includes compounds, compositions or materials that are Generally Recognized As Safe (GRAS). Therapeutic agents can be applied to skin, hair or nails of a subject or may be ingested, inhaled, injected, or otherwise introduced into the body of a subject.

A "cosmetic agent" is a compound, composition or formulation that is intended to be rubbed, poured, sprinkled, or sprayed on, introduced into, or otherwise applied to the body of a subject for cleansing, beautifying, promoting attractiveness, or altering the appearance. Cosmetic agents are typically applied to skin, hair or nails of a subject.

A "treated chitosan" is prepared by dialyzing chitosan against water and various salts and/or anionic solutions. The treated chitosans have structural conformations that are identifiably and reproducibly altered from untreated chitosan. The resulting treated chitosans exhibit changes in chemical, physical and/or performance properties or characteristics relative to untreated chitosan.

A "modified chitosan" is chitosan that has undergone chemical modifications through covalent attachments of one or more atomic structures, including single atom substitutions (such as fluorine in place of a hydrogen) or molecular structures, including functional groups, to the chitosan molecules. Modified chitosans also include chitosans that have been non-covalently associated with one or more distinct chemical modifiers, either atomic structures or molecular structures. Modified chitosans can also include chitosans that have co-additions of any number of distinct chemical modifiers, either atomic structures or molecular structures. Modified chitosans can also include a combination or mixture of the three above-identified classes of modified chitosans. Chemical modifiers are generally selected to impart a desired behavior, property or characteristic to the chitosan for a given application.

A "modified and treated chitosan" is chitosan that has undergone both modification and treatment as described above.

The "modified", "treated" and "modified and treated chitosan" are in the form of a solution of chitosan where the chitosan is homogeneously soluble in an aqueous solution. The "modified", "treated" and "modified and treated chitosan" are not in the form of particles (e.g. nanoparticles, coating particles, and the like).

The chitosan of the "modified", and "modified and treated chitosan" is covalently modified by the addition of charged groups, lipophilic groups, hydrophilic groups, cationic groups or anionic groups. In one or more instances, the covalent modification is at the 2-amino position of the glucosamine ring. In one example, the modification is of the primary amine. In one or more instances of the composition, the lipophilic group is an alkyl group. The alkyl group can be a straight chain alkyl or a branched chain alkyl group containing 4 to 30 carbons. In one or more instances of the composition, the non-polymeric anion is phosphate, citrate, pyro-phosphate, sulfate, iodide, bromide, chloride, nitrate, nitrite, oxalate, acetate, fluoride, chlorate, bromate, chlorite, formate, hydrogen phosphate, or dihydrogen phosphate. In one or more instances of the composition, the charged group is succinate (anionic), amino ethane (cationic), or amino propane (cationic). In one or more instances of the composition, the hydrophilic group is an alcohol. The alcohol can be ethanol or propanol. In one example, the modifying group is octane sulfonyl chloride. "Modified and treated chitosans" also include chitosans that have been non-covalently associated with one or more distinct chemical modifiers, either atomic structures or molecular structures. "Modified and treated chitosans" can also include chitosans that have co-additions of any number of distinct chemical modifiers, either atomic structures or molecular structures. "Modified and treated chitosans" can also include a combination or mixture of the three above-identified classes of modified chitosans.

The "modified", "treated" and "modified and treated chitosan" have an ionic balance, which is obtained by the addition of small, non-polymeric anions. Examples of such small, non-polymeric anions include, but are not limited to phosphate, citrate, pyro-phosphate, sulfate, iodide, bromide, chloride, nitrate, nitrite, oxalate, acetate, fluoride, chlorate, bromate, chlorite, formate, hydrogen phosphate, or dihydrogen phosphate. The "modified", "treated" and "modified and treated chitosan" does not contain polymeric anions. An example for such a polymeric material is hyaluronic acid.

U.S. Pat. No. 8,546,384 B2 (Bonding tissues and cross-linking proteins with naphthalimide compounds), US 2008/0200948 A1 (Novel biomaterials and a method for making and using same) and US 2016/0175449 A1 (Novel biomaterials and a method for making and using same) each of which are incorporated herein in their entireties for all purposes, describe compositions of treated, modified and modified and treated chitosan and their uses.

As used throughout, by a "subject" is meant an animal or human. Thus, a subject can include domesticated animals, such as cats, dogs, etc., livestock (e.g., cattle, horses, pigs, sheep, goats, etc.), laboratory animals (e.g., mouse, rabbit, rat, guinea pig, etc.) and birds. In one aspect, the subject is a mammal such as a primate or a human, including customers or patients.

Various test systems have been developed to identify chemicals which, upon topical exposure, could lead to adverse skin effects. The most commonly accepted such test, an in-vitro skin irritation assay using skin reconstructs (epidermal equivalents) was accepted by the European Union, and is now used worldwide. (https://ntp.niehs.nih.gov/iccvam/suppdocs/feddocs/oecd/oecd-tg439-2013-508.pdf). The test includes a standard negative control (NC, a non-irritant), and a standard positive control (PC, a strong irritant). The suggested PC chemical is aqueous SDS, and the suggested NC chemicals are water or phosphate buffered saline (PBS). SDS induces cell death and increases the secretion of inflammatory mediators (e.g. IL-1$\alpha$) in a dose-responsive manner.

IL-1$\alpha$ (interleukin-1 alpha, also named IL-1 alpha), is an inflammatory cytokine that serves as a biomarker for skin irritation. Topical agents that are skin irritants, represented by SDS and including e.g. retinoids, induce IL-1$\alpha$ secretion in a dose-responsive manner, and an experimental reduction in IL-1$\alpha$ secretion correlates with a reduction or amelioration of topical agent-induced skin irritation.

We have unexpectedly found that modified chitosan markedly reduced SDS-induced IL-1$\alpha$ secretion and cell death in skin cells. Additionally, the modified chitosan markedly reduced retinoid-induced, and chymotrypsin-induced IL-1$\alpha$ secretion and cell death in vitro. This suggests that the modified chitosan could be used in topical preparations to reduce skin irritation.

The skin areas that could be treated by the compositions of this invention include any skin area that could be treated with a topical agent or product, including, but not limited to, the scalp, face, head, neck, chest, back, arms, legs, diaper area, underaims area, and the like. The compositions of this invention may be used, but are not limited to, cosmetically or pharmaceutically accepted forms and carriers such as solutions, suspensions, emulsions (including micro-emulsions and nano-emulsions), lotions, creams, gels, sticks, sprays, ointments, cleansing liquids, washes, solid bars, shampoos, hair conditioners, pastes, foams, powders, mousses, shaving creams, shaving gels, wipes, patches, hydrogels, film-forming products, masks, liquid drops, muco-adhesives, and the like. The precise concentrations, effects of the composition and methods of this invention will vary with the area being treated, the age, health and skin type of the end user, the duration and nature of the treatment, the specific composition employed, the particular condition being treated, the particular cosmetically- or pharmaceutically-acceptable carrier utilized, and like factors.

EXAMPLES

Example 1: SDS-Induced Irritation

An In Vitro Skin Irritation Test was performed according to OCED guidelines. Irritant materials are identified by their ability to decrease cell viability below a defined threshold level of 50%. Moreover, if the cytotoxic effect is absent or weak, a quantifiable amount of inflammatory mediators (e.g. IL-1$\alpha$) is released by the epidermis and may be used in a tiered approach to increase the sensitivity of the test.

Test materials (30 μl) were topically applied onto three-dimensional human epidermal equivalents (EPI-200 from MatTek, Ashland, Mass.), n=3 tissues per treatment group. Test materials included a positive control irritant (5% sodium dodecyl sulfate, SDS), and a negative control (Phosphate Buffered Saline, PBS), and aqueous SDS solutions of 0.2, 0.4 and 0.6%, with or without the addition of modified chitosan (1%). Modified chitosan (1%) alone was also included.

After a 60 minute exposure, the tissues were rinsed with PBS and were transferred to fresh medium. After 24 hours, media was collected for IL-1$\alpha$ analysis and tissues were transferred to fresh media for an additional 18 hr to allow the toxic effect of irritant chemicals to develop. After the 42 hr post-exposure equilibration, media was again collected and tissue viability was determined using an MTT assay.

As shown by the MTT assay (Table 1), all test materials resulted in viabilities well above the 50% cut-off, and were all at about the same viability levels as the PBS (negative control)-treated tissues (~100-110%). One exception was the 0.6% SDS-treated tissues that were ~90% dead. However, In the presence of the modified chitosan, the 0.6% SDS had no negative effect on cell viability, demonstrating a rescue of the cell death effect by the modified chitosan.

TABLE 1

Tissue viability assay upon SDS exposure

| | mean of viability [%] | SD of viability |
|---|---|---|
| NC (PBS) | 100.0 | 10.28 |
| PC (5% SDS) | 11.1 | 0.87 |
| 0.2% SDS | 110.0 | 4.00 |
| 0.4% SDS | 106.3 | 4.76 |
| 0.6% SDS | 13.8 | 4.51 |
| 1% OsC | 105.3 | 4.61 |
| 0.2% SDS + 1% modified chitosan | 110.5 | 0.82 |
| 0.4% SDS + 1% modified chitosan | 104.4 | 1.53 |
| 0.6% SDS + 1% modified chitosan | 109.8 | 4.75 |

IL-1α secretion was analyzed using the Human IL-1α ELISA Duo Set (R&D Systems, cat #DY200, Lot 1353857). A Bio-Tek microplate reader and KC4 software were used for sample analysis. The results of the IL-1α analysis, which are used to increase the sensitivity of the test, are shown in Table 2.

As shown in Table 2, SDS exposure resulted in a dose-dependent increase in IL-1α secretion. However, in the presence of the modified chitosan, the SDS, even at the 0.6% concentration, did not induce IL-1α secretion. These data demonstrate the ability of the modified chitosan to reduce and ameliorate SDS-induced skin irritation. As SDS is considered a model system for skin irritation, these data suggest that the modified chitosan could reduce tissue death and reduced skin irritation induced by any topical irritating agent.

TABLE 2

IL-1α secretion upon SDS exposure

| | Avg | StDev |
|---|---|---|
| NC | 23.48 | 1.84 |
| PC | 425.23 | 55.43 |
| 0.2% SDS | 151.98 | 43.00 |
| 0.4% SDS | 334.95 | 80.16 |
| 0.6% SDS | 524.61 | 0.00 |
| 1% modified chitosan | 32.44 | 1.40 |
| 0.2% SDS + 1% modified chitosan | 29.14 | 8.86 |
| 0.4% SDS + 1% modified chitosan | 32.32 | 10.45 |
| 0.6% SDS + 1% modified chitosan | 18.97 | 1.45 |

This example suggests that the used of modified chitosan in topical formulations could ameliorate topical agent-induced skin irritation and tissue damage.

Example 2: Retinoid-Induced Irritation

A standard In Vitro Skin Irritation Test was performed according to OCED guidelines. Test materials (30 μl) were topically applied onto three-dimensional human epidermal equivalents (EPI-200 from MatTek, Ashland, Mass.), n=3 tissues per treatment group. Test materials included a positive control irritant (5% sodium dodecyl sulfate, SDS), and a negative control (Phosphate Buffered Saline, PBS), Retinol (0.01-1%) combined with 1% of the modified chitosan, and Retinoic acid (0.01-1%) combined with 1% of the modified chitosan. Retinoids were dissolved in one of two vehicles: V1 (50% ethanol, 20% glycerin, 0.1% BHT, in PBS) or V2 (50% ethanol, 0.1% BHT, in PBS).

After a 60 minute exposure, the tissues were rinsed with PBS and were transferred to fresh medium. After 24 hours, media was collected for IL-1α analysis and tissues were transferred to fresh media for an additional 18 hr to allow the toxic effect of irritant chemicals to develop. After the 42 hr post-exposure equilibration, media was again collected and tissue viability was determined using an MTT assay.

As shown by the MTT assay, all test materials resulted in viabilities well above the 50% cut-off, and were all at about the same viability levels as the PBS (negative control)-treated tissues (95-110%). As expected, the positive control irritant resulted in less than 10% viability. Therefore, all test agent combinations (all containing the modified chitosan) are considered as non-irritants according to the ECVAM guidelines.

IL-1α secretion was analyzed using the Human IL-1α ELISA Duo Set (R&D Systems, cat #DY200, Lot 1353857). A Bio-Tek microplate reader and KC4 software were used for sample analysis. The results of the IL-1α analysis, which are used to increase the sensitivity of the test, are shown in Table 3.

TABLE 3

Summary of IL-1α levels 24 hr post-exposure

| | | AVG | STD DEV |
|---|---|---|---|
| Negative Control | PBS | 28.32 | 23.53 |
| Positive Control | 5% SDS | >524.6 | |
| In V1 | Modified chitosan (1%) + Retinol (1%) | 23.12 | 11.58 |
| In V1 | Modified chitosan (1%) + Retinol (0.35%) | 36.02 | 17.23 |
| In V1 | Modified chitosan (1%) + Retinol (0.1%) | 24.22 | 9.94 |
| In V1 | Modified chitosan (1%) + Retinol (0.04%) | 33.55 | 15.78 |
| In V1 | Modified chitosan (1%) + Retinol (0.01%) | 31.58 | 14.21 |
| In V1 | Modified chitosan (1%) + Retinoic acid (1%) | 19.06 | 8.92 |
| In V1 | Modified chitosan (1%) + Retinoic acid (0.35%) | 24.12 | 16.07 |
| In V1 | Modified chitosan (1%) + Retinoic acid (0.1%) | 28.49 | 17.73 |
| In V1 | Modified chitosan (1%) + Retinoic acid (0.04%) | 22.84 | 2.51 |
| In V1 | Modified chitosan (1%) + Retinoic acid (0.01%) | 35.14 | 13.90 |
| In V2 | Modified chitosan (1%) + Retinol (1%) | 34.76 | 5.66 |
| In V2 | Modified chitosan (1%) + Retinol (0.35%) | 21.76 | 0.57 |
| In V2 | Modified chitosan (1%) + Retinol (0.1%) | 14.80 | 3.71 |

TABLE 3-continued

Summary of IL-1α levels 24 hr post-exposure

| | | AVG | STD DEV |
|---|---|---|---|
| In V2 | Modified chitosan (1%) + Retinol (0.04%) | 26.69 | 5.51 |
| In V2 | Modified chitosan (1%) + Retinol (0.01%) | 32.62 | 4.80 |
| In V2 | Modified chitosan (1%) + Retinoic acid (1%) | 28.83 | 10.13 |
| In V2 | Modified chitosan (1%) + Retinoic acid (0.35%) | 29.61 | 9.65 |
| In V2 | Modified chitosan (1%) + Retinoic acid (0.1%) | 41.82 | 6.44 |
| In V2 | Modified chitosan (1%) + Retinoic acid (0.04%) | 23.82 | 18.79 |
| In V2 | Modified chitosan (1%) + Retinoic acid (0.01%) | 22.89 | 13.83 |

As shown in Table 3, all test articles resulted in IL-1α secretion that was similar to that of the negative control. These results document that in the presence of the modified chitosan, the retinoids, even at as high concentration as 1%, are not inducing IL-1α secretion. These data confirm the ability of the modified chitosan to reduce and ameliorate the known retinoid-induced skin irritation.

Example 3: Retinoid-Induced Irritation—Long Term Exposure and Treatment

Epidermal equivalents (EPI-200 from MatTek, Ashland, Mass.) were topically treated daily, for four days, with 30 μl of each test article, n=3 tissues per treatment group. Test articles were removed from the apical surface of the tissue daily by washing with PBS prior to reapplication of test article. Tissues were fed daily with 0.9 mL EPI-100-NMM. Tissues remained untreated, or treated with a vehicle (45% ethanol, 0.1% BHT, in PBS), without and with increasing concentrations of retinol (0.01-1%), with or without the addition of the modified chitosan (1%).

Visual observations at 96 hour post treatment documented that the 1% retinol-treated tissues were partially disintegrated, and resembled tissues that were exposed to a harsh toxic agent. Interestingly, when the tissues were exposed to 1% retinol that was combined with the modified chitosan, they were visually similar to the untreated controls, and did not look disintegrated or negatively affected.

This example indicates that the addition of the modified chitosan to topical preparations with high retinoid concentrations protects the tissue from retinoid-induced negative and destructive effects.

Example 4: Retinoid-Induced Irritation—Long Term Exposure and Treatment

Epidermal equivalents (EPI-200 from MatTek, Ashland, Mass.) were topically treated daily, for four days, with 30 μl of each test article, n=3 tissues per treatment group. n=3 tissues were left untreated. Test articles were removed from the apical surface of the tissue daily by washing with PBS prior to reapplication of test article. Tissues were fed daily with 0.9 mL EPI-100-NMM. Treatments include retinol, 0.01-1%, in an irritant vehicle (45% ethanol, 0.1% BHT, in PBS), with and without 1% modified chitosan.

Media was collected at 96 hour post treatment and IL-1α concentration was analyzed using the Human IL-1α ELISA Duo Set (R&D Systems, cat #DY200, Lot 1353857). A Bio-Tek microplate reader and KC4 software were used for sample analysis.

The results of the IL-1α secretion analysis are documented in Table 4.

TABLE 4

Summary of IL-1α levels at 96 hr post-exposure

| | Tissue 1 | Tissue 2 | Tissue 3 | AVG | STD DEV |
|---|---|---|---|---|---|
| Untreated | 26.35 | 21.19 | 35.45 | 27.66 | 7.22 |
| Vehicle | 104.66 | 124.25 | 108.67 | 112.53 | 10.35 |
| Vehicle + retinol (1%) | 885.52 | 1097.75 | 1078.11 | 1020.46 | 117.27 |
| Vehicle + retinol (0.1%) | 351.17 | 108.86 | 262.00 | 240.68 | 122.55 |
| Vehicle + retinol (0.01%) | 124.24 | 108.54 | 81.94 | 104.90 | 21.38 |
| Vehicle + modified chitosan | 209.16 | 67.40 | 84.03 | 120.20 | 77.49 |
| Vehicle + modified chitosan + retinol (1%) | 250.94 | 331.86 | 589.33 | 390.71 | 176.71 |
| Vehicle + modified chitosan + retinol (0.1%) | 107.48 | 86.87 | 178.39 | 124.24 | 48.01 |
| Vehicle + modified chitosan + retinol (0.01%) | 92.38 | 208.75 | 221.74 | 174.29 | 71.23 |

The results documented in Table 4 show that retinol induces skin irritation in a dose-responsive manner, as documented with the IL-1α secretion biomarker. The addition of the modified chitosan only to the vehicle does not induce or stimulate IL-1α secretion from the treated epidermal equivalents, confirming that the modified chitosan, by itself, does not induce skin irritation. Additionally, the modified chitosan markedly (~60%) reduced the retinol (1%)-induced IL-1α secretion, and a similar reduction (~50%) was observed for the 0.1% retinol-treated tissues. These results indicate that the addition of the modified chitosan to topical retinoid preparations significantly reduces retinoid-induced skin irritation.

Example 5: Diaper Rash Irritation

A standard In Vitro Skin Irritation Test was performed according to OCED guidelines. The method is described in Example 1. Test articles included Chymotrypsin (0.005, 0.01 and 0.02%), with and without modified chitosan (1%). Chymotrypsin is the major fecal irritant enzyme that initiates diaper rash.

The exposure to these representative fecal concentrations of chymotrypsin, for one hour, did not induce cell death.

As shown in Table 5, chymotrypsin exposure resulted in a dose-dependent increase in IL-1α secretion, documenting the irritation induced by this fecal enzyme. Treatment of the tissues with the modified chitosan prior to enzyme exposure markedly reduced IL-1α secretion, documenting a protective effect of the modified chitosan from a chronic exposure to irritants.

TABLE 5

| IL-1α secretion upon chymotrypsin exposure | | | | | | |
|---|---|---|---|---|---|---|
| Conditions | tissue 1 | tissue 2 | tissue 3 | AVG | ST. DEV | Ttest |
| Untreated Control | 47.360 | 49.380 | 24.667 | 40.469 | 13.722 | |
| Positive Control (PC, 5% SDS) | 459.595 | 384.839 | 337.908 | 394.114 | 61.371 | 0.001 |
| Untreated + culture medium | 28.561 | 37.492 | 53.160 | 39.738 | 12.452 | 0.949 |
| Untreated + Chymotrypsin (0.005%) | 47.295 | 74.241 | 74.302 | 65.279 | 15.575 | 0.107 |
| Untreated + Chymotrypsin (0.01%) | 58.421 | 53.293 | 87.502 | 66.405 | 18.449 | 0.122 |
| Untreated + Chymotrypsin (0.02%) | 67.307 | 353.378 | 79.779 | 166.821 | 161.683 | 0.249 |
| Modified chitosan | 32.227 | 30.121 | 86.467 | 49.605 | 31.941 | 0.673 |
| Modified chitosan + culture medium | 51.169 | 22.234 | 47.471 | 40.291 | 15.747 | 0.989 |
| Modified chitosan + Chymotrypsin (0.005%) | 38.861 | 71.009 | 81.859 | 63.909 | 22.361 | 0.197 |
| Modified chitosan + Chymotrypsin (0.01%) | 154.138 | 58.447 | 39.682 | 84.089 | 61.385 | 0.296 |
| Modified chitosan + Chymotrypsin (0.02%) | 66.625 | 153.270 | 96.796 | 105.564 | 43.983 | 0.071 |

These results indicate that treatment with the modified chitosan before exposure to a chronic irritant significantly reduces irritant-induced skin irritation. These results suggest that the use of modified chitosan in diaper rash prevention products could protect the skin from diaper rash inducing agents and reduce skin irritation in the diaper area.

Example 6: UV Irritation

Epidermal equivalents (EPI-200 tissues, MatTek, Ashland Mass.) were topically treated with 30 μl of modified chitosan (1% OsC) and were allowed to dry for 60 minutes. UVA/UVB-irradiation was performed using a Honle SOL500 Solar Simulator. The duration of irradiation and the doses were determined using only the UVB wavelength. Tissues were exposed to increasing doses of UVB-irradiation (100, 250, and 400 mJ/cm$^2$ UVB). n=12 tissues (n=6 with test material and n=6 untreated) were exposed to each dose and n=6 tissues (n=6 with test material and n=6 untreated) were sham irradiated (See Table 6a for a list of all treatment groups).

Following irradiation, tissues were incubated at 37° C./5% CO2 for 24 hrs. After 24 hours, tissue viability was quantified by MTT and media was collected for measurement of IL-1α release by ELISA. IL-1 alpha concentration was analyzed using the Human IL-1α ELISA (R&D Systems, cat #DY200, Lot #325259). A Bio-Tek microplate reader and Gen5 software were used for sample analysis.

TABLE 6a

| UV Treatment Groups | | |
|---|---|---|
| Treatment Group | Test Formulation | UVB dose |
| 1 | Untreated | Sham-irradiated |
| 2 | Untreated | 100 mJ/cm$^2$ |
| 3 | Untreated | 250 mJ/cm$^2$ |
| 4 | Untreated | 400 mJ/cm$^2$ |
| 5 | Polymer | Sham-irradiated |
| 6 | Polymer | 100 mJ/cm$^2$ |
| 7 | Polymer | 250 mJ/cm$^2$ |
| 8 | Polymer | 400 mJ/cm$^2$ |

The results indicate that tissue viability of tissues treated with the modified chitosan was comparable in sham-irradiated tissues and those exposed to UVB-irradiation (100-400 mJ/cm2).

The results of the IL-1α analysis are shown in table 6b, and the associated statistical analysis is shown in table 6c. As documented in this study, the levels of IL-1α were similar in sham-irradiated tissues compared to tissues exposed to 100 mJ/cm2 and 250 mJ/cm2 UVB. A significant increase in IL-1α levels was observed in tissues exposed to 400 mJ/cm2. This increase was significantly reduced with the pretreatment with the modified chitosan.

These results indicate that the pretreatment of skin with a modified chitosan prior to UV exposure result in reduced IL-1α secretion. Therefore, the modified chitosan is able to mitigate part of the inflammatory response and irritation activity induced by UV irradiation.

TABLE 6b

| IL-1α Levels 24 hours post exposure | | | |
|---|---|---|---|
| Treatment group # | Condition | Mean IL-1α (pg/mL) | SD |
| 1 | Untreated - Sham | 65.41 | 20.90 |
| 5 | +Polymer1 - Sham | 61.58 | 21.75 |

TABLE 6b-continued

| IL-1α Levels 24 hours post exposure | | | |
|---|---|---|---|
| Treatment group # | Condition | Mean IL-1α (pg/mL) | SD |
| 2 | Untreated - 100 mJ/cm$^2$ | 47.06 | 22.86 |
| 6 | +Polymer1 - 100 mJ/cm$^2$ | 68.13 | 13.90 |
| 3 | Untreated - 250 mJ/cm$^2$ | 70.35 | 10.18 |
| 7 | +Polymer1 - 250 mJ/cm$^2$ | 69.03 | 12.63 |
| 4 | Untreated - 400 mJ/cm$^2$ | 189.89 | 6.50 |
| 8 | +Polymer1 - 400 mJ/cm$^2$ | 130.94 | 27.02 |

TABLE 6c

| Student's t-test (compared to Untreated-Sham) | | |
|---|---|---|
| Treatment group # | Condition | p-value |
| 1 | Untreated - Sham | |
| 5 | +Polymer1 - Sham | 0.86 |
| 2 | Untreated - 100 mJ/cm$^2$ | |
| 6 | +Polymer1 - 100 mJ/cm$^2$ | 0.08 |
| 3 | Untreated - 250 mJ/cm$^2$ | |
| 7 | +Polymer1 - 250 mJ/cm$^2$ | 0.85 |
| 4 | Untreated - 400 mJ/cm$^2$ | |
| 8 | +Polymer1 - 400 mJ/cm$^2$ | 0.0004 |

What is claimed is:

1. A composition comprising:

(a) at least one topical irritating agent comprising a retinoid, a retinoid derivative, or a retinoid precursor, wherein the retinoid, retinoid derivative and the retinoid precursor are selected from the group consisting of retinol, retinal, retinyl esters, tretinoin, retinoic acid, Vitamin A, ester of Vitamin A, isotretinoin, alitretinoin, etretinate, acitretin, adapalene, bexarotene, and tazarotene, and combinations thereof, and (b) at least one chitosan covalently modified with octane sulfonic acid via sulfonamide linkage, and wherein the composition provides a reduction in skin irritation and/or a reduction in skin inflammation and/or a reduction in irritant-induced IL-1α secretion after contact with the composition compared with a control composition comprising the topical irritating agent but not the chitosan.

2. The composition of claim 1, wherein said retinoid, retinoid precursor or retinoid derivative comprises retinol.

3. The composition of claim 1, wherein said retinoid, retinoid precursor or retinoid derivative comprises about 0.001-5% W/V of the total weight of the composition.

4. The composition of claim 1, wherein said at least one chitosan covalently modified with octane sulfonic acid comprises about 0.0001-5% W/V of the total weight of the composition.

5. The composition of claim 1, wherein the ester of Vitamin A is retinol-palmitate.

* * * * *